United States Patent
Fishman et al.

(10) Patent No.: US 8,793,142 B2
(45) Date of Patent: Jul. 29, 2014

(54) METHODS AND APPARATUSES FOR REMOTE DIAGNOSIS AND PRESCRIPTION

(76) Inventors: Harvey Abraham Fishman, Menlo Park, CA (US); Michael Joseph Dacey, Jr., Menlo Park, CA (US); Tamer Abuelata, Cupertino, CA (US)

( * ) Notice: Subject to any disclaimer, the term of this patent is extended or adjusted under 35 U.S.C. 154(b) by 0 days.

(21) Appl. No.: 13/267,727

(22) Filed: Oct. 6, 2011

(65) Prior Publication Data

US 2013/0090938 A1    Apr. 11, 2013

(51) Int. Cl.
*G06Q 50/00* (2012.01)

(52) U.S. Cl.
USPC .................................. 705/2; 705/3; 600/300

(58) Field of Classification Search
CPC ......... G06F 19/322; G06F 3/01; G06F 3/013; G06F 3/04842; G06Q 50/22; G06Q 50/24
USPC .......................................... 705/2–3; 600/300
See application file for complete search history.

(56) References Cited

U.S. PATENT DOCUMENTS

| 7,156,809 | B2* | 1/2007 | Quy .............................. 600/301 |
| 7,244,231 | B2* | 7/2007 | Dewing et al. ................ 600/300 |
| 2009/0132275 | A1* | 5/2009 | Jung et al. ......................... 705/2 |
| 2010/0114602 | A1* | 5/2010 | Joao et al. ......................... 705/2 |
| 2010/0121156 | A1* | 5/2010 | Yoo .............................. 600/300 |
| 2010/0292999 | A1* | 11/2010 | Verma ............................... 705/2 |
| 2011/0082704 | A1* | 4/2011 | Blum ................................ 705/2 |

* cited by examiner

*Primary Examiner* — Sind Phongsvirajati
(74) *Attorney, Agent, or Firm* — Dickstein Shapiro LLP

(57) ABSTRACT

A method of enabling remote medical diagnosis of a medical condition comprising: providing a software application for a mobile device designed to: provide a graphical user interface on a display of the mobile device wherein the graphical user interface is designed to allow a patient to collect data for use in the medical diagnosis of the medical condition; communicate the data from the mobile device to a medical professional; and receive a medical diagnosis from the medical professional.

23 Claims, 11 Drawing Sheets

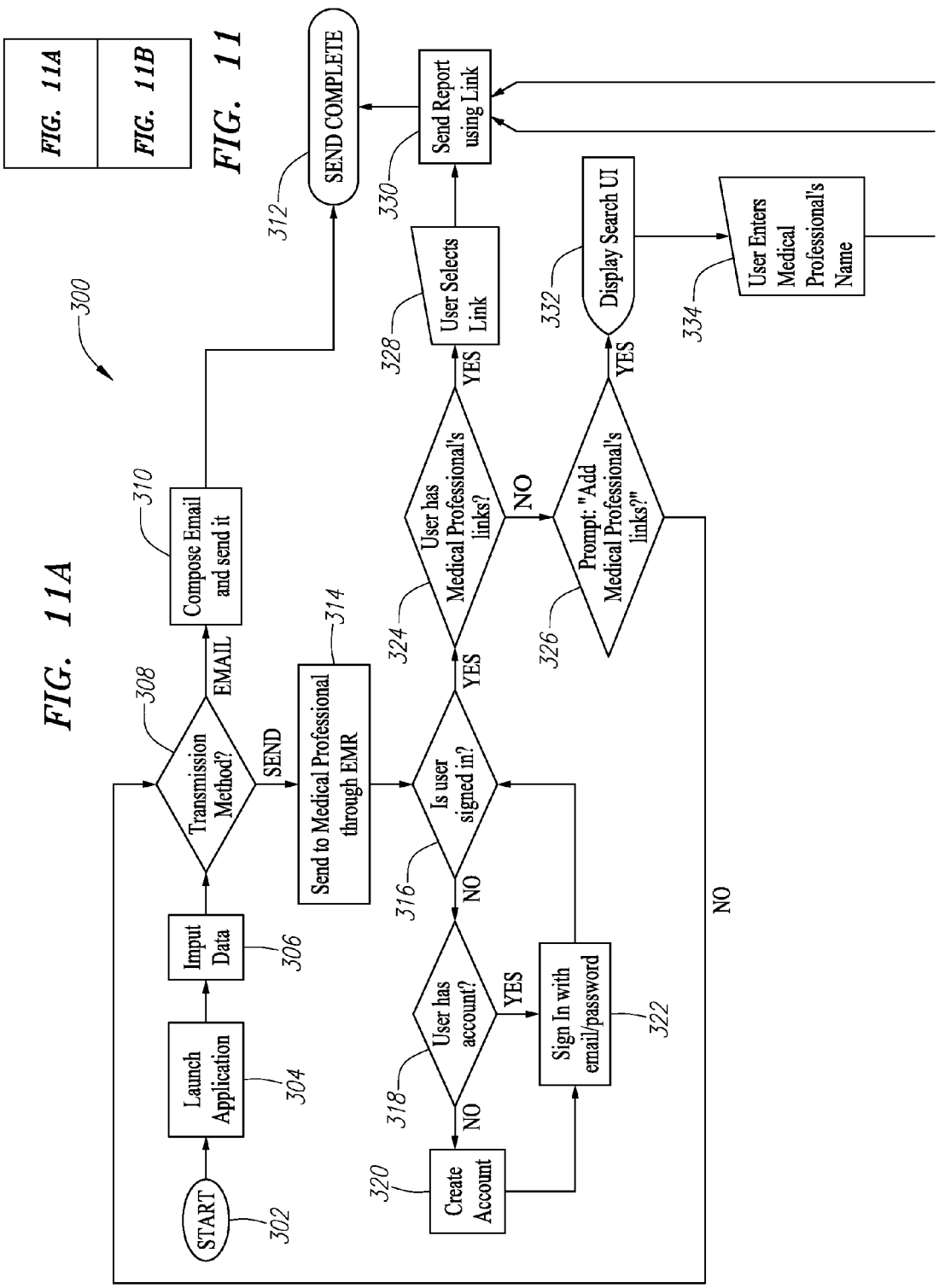

METHODS AND APPARATUSES FOR REMOTE DIAGNOSIS AND PRESCRIPTION

FIELD

The present patent document relates to methods and apparatuses for remote diagnosis and prescription. In particular, the present patent document relates to software for mobile devices to allow patients to attain medical diagnosis and prescription remotely.

BACKGROUND

Many people have nagging or reoccurring injuries or illnesses. In addition, frequently people may think they have some kind of health issue when in fact nothing is really wrong at all. For example, many people may wonder about changes in a spot of pigment on their skin or redness in their eyes. The uncertainty of not knowing whether something is a problem may be very stressful.

In actuality, often times these injuries or illnesses are not severe and do not pose a real threat to the person's health. However, sometimes these injuries should be reviewed by a medical professional to ensure their insignificance. At a minimum, a review by a medical professional would allow the person suffering to feel more secure. In addition, many remedial injuries or illnesses may be better treated with medicine which requires a prescription from a medical professional.

In some of these circumstances, it may be a huge inconvenience for the person to repeatedly make appointments with a doctor to be examined or reexamined for the same thing. Furthermore, it may be extremely costly to the patient and the insurance involved to have a patient repeatedly at the doctor's office. In addition, doctors are increasingly pressured to see more patients and need improved efficiency in office work flow. This pertains not only to patients in remote locations, but patients waiting in the medical professional's office. A huge amount of time is wasted by patients filling out paperwork or waiting to see the physician.

To this end it would be beneficial to have methods and apparatuses that would allow a patient to provide enough information to a remotely located medical professional so that the medical professional could diagnose and/or prescribe treatment for the patient. These methods and apparatuses could also enhance the in-office patient visit.

SUMMARY

In view of the foregoing, one aspect of the various disclosed embodiments in the present patent document is to provide improved methods and apparatuses for allowing remote diagnosis of patients by medical professionals and allowing the medical professionals to respond to the patients with a prescription or treatment suggestion(s). Preferably the methods and apparatuses address, or at least ameliorate, one or more of the problems described above. To this end, a method for enabling remote medical diagnosis of a medical condition is provided. The method comprises providing a software application for a mobile device designed to: provide a graphical user interface on a display of the mobile device wherein the graphical user interface is designed to allow a patient to collect data for use in the medical diagnosis of the medical condition; communicate the data from the mobile device to a medical professional; and receive a medical diagnosis from the medical professional.

In various different embodiments, the data collected for use in a diagnosis may be many different types of data including, photographs, video, sound recordings, text, selections from provided lists and numerous other types of data. Some embodiments may include data that is the results of various diagnostic tests run by or on the mobile device. The data may be related to symptoms, the timing of the symptoms, the location of the symptoms, or any other type of data helpful in allowing a medical professional to make a diagnosis and/or prescribe treatment.

The embodiments described herein may be applied to any type of medical condition. In a preferred embodiment, the medical condition may relate to the eye, and the data may be routed to an ophthalmologist. In another preferred embodiment, the medical condition may relate to the skin, and the data is directed to a dermatologist. However, in other embodiments, many other medical conditions may be targeted. In some embodiments, more than one medical condition may be targeted, and the patient may select the appropriate medical conditions.

In one embodiment, the data is communicated to the medical professional via email. In other embodiments, the data may be communicated using other methods such as text message or direct upload to an electronic medical record system (EMR). In some embodiments, the communication may be a secure communication in the form of encrypted data or a secure connection or both.

In a preferred embodiment, the software application may not only allow diagnosis of a medical condition but may also allow the medical professional to submit a prescription to the patient. In other embodiments, the software application allows the medical professional to order or have delivered a sample prescription medicine that can be from the drug company or pharmacy. In yet other embodiments, the patient may be able to order or have delivered a sample prescription. In such embodiments, the sample prescription may be delivered by the company, picked up at a pharmacy, or sent directly to the patient's house. The sample may consist of an over the counter medicine, sunscreen, vitamin, facial cream, etc., or may be something that requires a medical professional's prescription.

Another aspect of the present patent document provides a computer readable medium containing program instructions for providing a remote diagnosis to a patient by a medical professional. The execution of the program instructions by one or more processors of a mobile device causes the one or more processors to carry out the steps of: providing a graphical user interface for collecting data for use in a medical diagnosis on a display of the mobile device; communicating the data from the mobile device to a medical professional; and receiving a medical diagnosis from the medical professional.

In some embodiments, the graphical user interface includes an element which initiates taking a picture of a medical condition. In other embodiments, the graphical user interface includes a representation of at least a portion of a body designed to allow indication of a location of a medical condition.

In yet another aspect of the present patent document, a method of enabling remote medical diagnosis of a medical condition is provided. The method comprises: capturing data for use in a medical diagnosis via components of a mobile device; communicating the data from the mobile device to a medical professional; and receiving a medical diagnosis from the medical professional.

In yet another aspect of the present patent document, a mobile device is provided. The mobile device comprises: memory; one or more processors in communication with the memory; a display; a software application residing in the memory that when executed by one or more processors causes the mobile phone to perform the following steps: display a graphical user interface on the display which allows the user to input data regarding a current medical condition; and communicate the data to a medical professional.

The apparatuses and methods for remote diagnosis and prescription described herein provide benefits over other methods and apparatuses. Further aspects, objects, desirable features, and advantages of the devices and methods disclosed herein will be better understood from the detailed description and drawings that follow in which various embodiments are illustrated by way of example. It is to be expressly understood, however, that the drawings are for the purpose of illustration only and are not intended as a definition of the limits of the claimed embodiments.

BRIEF DESCRIPTION OF THE DRAWINGS

FIG. 11A illustrates the top half of a flow chart of one embodiment of a process that communicates data for use in a diagnosis and/or prescription to a medical professional.

DETAILED DESCRIPTION OF THE EMBODIMENTS

Figure 1:
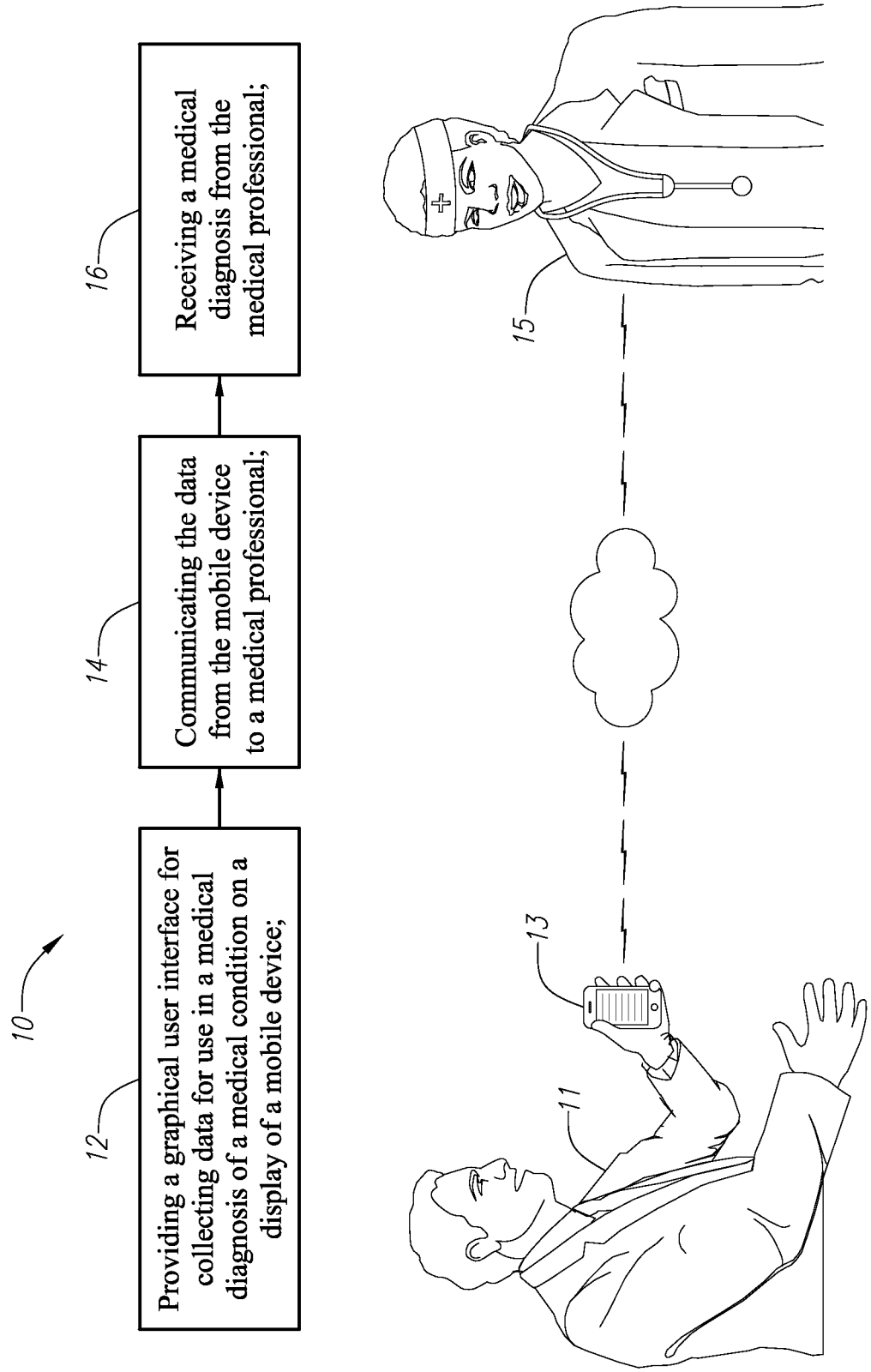
FIG. 1 illustrates one embodiment of a method of enabling remote medical diagnosis of a medical condition.

The following detailed description includes representative examples utilizing numerous features and teachings, both separately and in combination, and describes numerous embodiments in further detail with reference to the attached drawings. This detailed description is merely intended to teach a person of skill in the art further details for practicing preferred aspects of the present teachings and is not intended to limit the scope of the claims. Therefore, combinations of features disclosed in the following detailed description may not be necessary to practice the teachings in the broadest sense, and are instead taught merely to describe particularly representative examples of the present teachings.

Some portions of the detailed descriptions that follow are presented in terms of algorithms and sequences of operations which are performed within a computer memory. These algorithmic descriptions and representations are the means used by those skilled in the data processing arts to most effectively convey the substance of their work to others skilled in the art. An algorithm or sequence of operations is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing," "computing," "calculating," "determining," "displaying" or the like, refer to the action and processes of a computer system, or similar electronic device, that manipulates and transforms data represented as physical (electronic) quantities within the computer system's registers and memories into other data similarly represented as physical quantities within the electronic device's memory or registers or other such information storage, transmission or display devices.

The embodiments disclosed also relate to an apparatus for performing the operations herein. This apparatus may be specially constructed for the required purposes, or it may comprise a general purpose processor selectively activated or reconfigured by a computer program stored in the electronic device. Such a computer program may be stored in a computer readable storage medium, such as, but is not limited to, any type of disk, including floppy disks, optical disks, CD-ROMs, and magnetic-optical disks, read-only memories (ROMs), random access memories (RAMs), EPROMs, EEPROMs, Flash memory, magnetic or optical cards, or any type of media suitable for storing electronic instructions, and each coupled to a computer system bus.

The algorithms presented herein are not inherently related to any particular electronic device or other apparatus. Various general purpose systems may be used with programs in accordance with the teachings herein, or it may prove convenient to construct a more specialized apparatus to perform the required method steps. The required structure for a variety of these systems will appear from the description below. It will be appreciated that a variety of programming languages may be used to implement the teachings of the embodiments as described herein.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help understand how the present teachings are practiced, but not intended to limit the dimensions and the shapes shown in the examples.

The present patent document describes unique methods and apparatuses to allow medical professionals to remotely diagnosis and prescribe treatment to patients. In a preferred embodiment, a software application is provided which runs on a mobile device such as a mobile phone. The software application may provide a patient with instructions on how to collect the necessary information a medical professional needs to make a remote diagnosis and/or prescribe treatment.

The instructions may come in the form of a graphical user interface (GUI). As just one example, the patient may be instructed by the mobile application to take a picture or a plurality of pictures of the area of interest. Once the necessary data is collected, the mobile software application facilitates providing the data to a medical professional, for example a doctor, who may use the data to provide a diagnosis and/or prescription to the patient without actually seeing the patient.

In some embodiments, the methods and apparatuses may be used to make a patient's visit to a medical professional's office more efficient. For example, the patient may fill out medical information or data for use in a diagnosis on his/her mobile device while waiting in the office of the medical professional. The medical information or data may include symptoms, pictures, video, tests designed to obtain information, personal information, or any other type of data the medical professional might need. Of course, the inputting of this information may even occur prior to the patient's arrival at the medical professional's office. In addition, the information may include disclaimers or other legal documents the patient may need to sign before being consulted by a medical professional.

FIG. 1 illustrates one embodiment of a method 10 of enabling a medical diagnosis of a medical condition. The embodiment shown in FIG. 1 includes: providing a GUI for collecting data for use in a medical diagnosis on a display of a mobile device 12; communicating the data from the mobile device to a medical professional 14; and receiving a medical prescription from the medical professional 16.

The method 10 enables remote medical diagnosis. A remote diagnosis includes any situation where the patient 11 is not physically present with the medical professional 15. In some embodiments, the medical professional 15 may be located in close proximity to the patient 11 but not physically in the same room. For example, the patient may be waiting in the medical professional's waiting room and using the method to begin collecting the information for use in a diagnosis or other important information related to the patient's medical history. In a preferred embodiment, the medical professional 15 and the patient 11 may be physically quite far apart. As just one example, the patient 11 may be going about his/her normal daily activities and the medical professional 15 may be in his/her office.

A medical diagnosis or medical condition includes anything related to a person's health. In a preferred embodiment, the medical diagnosis or medical condition may be related to symptoms of the eye or skin. However in other embodiments, a medical diagnosis or medical condition may be related to the common cold, cancer, pulled muscles, sore throats, heart attacks, tonsils, bones, cosmetics, pets, teeth, medications, neurological conditions, chiropractic conditions or any other health related ailment. A medical diagnosis includes even a partial diagnosis. For example, a medical professional may simply respond that the symptoms are not of significant concern or may respond that the patient 11 needs to seek a physical visit to a medical professional 15 without actually diagnosing the medical condition.

In a preferred embodiment, the mobile device 13 may be a mobile phone. In an even more preferable embodiment, the mobile device may be a smart-phone such as the iPhone®, Blackberry®, Android® based phone, or one of many other smart-phones. However in other embodiments, mobile device 13 may be any mobile device including a computer, laptop, mobile tablet, personal data assistant (PDA) or any other type of mobile device.

In a preferred embodiment, the medical professional 15 is a doctor. However in other embodiments, the medical professional 15 may be a nurse, chiropractor, physician's assistant, pharmacist or any other type of person who makes a profession providing health related diagnosis and/or prescribing treatment. The medical professional 15, may specialize in any medical field or may provide general medical services.

The patient 11 may be any person desirous of obtaining medical advice about a medical condition. In some embodiments, the patient 11 and the medical professional 15 may have a preexisting relationship. In other embodiments, the patient 11 and the medical professional 15 may not know each other.

The data may be communicated from the mobile device to the medical professional 15 in a number of different ways. For example, the mobile device may send an email to the medical professional, or a Short Message Service (SMS) message. In embodiments where the mobile device is a phone or provides phone service such as through Google voice, Skype or other internet phone software, the patient 11 may call the medical professional. The call may be in addition to sending data, or the data may be sent without a call from the patient. The data may also be uploaded to an intermediate location where the medical professional can view it such as a server on the Internet or other third party location.

The software application may be embodied in any number of formats. In a preferred embodiment, the software application is in the form of an application for a mobile device. However, other embodiments may be embodied in other forms or formats. For example, one embodiment of the software application may be in the form of a web page. The web page may be accessed and displayed on the mobile device via a data communication network such as the Internet.

Figure 2:
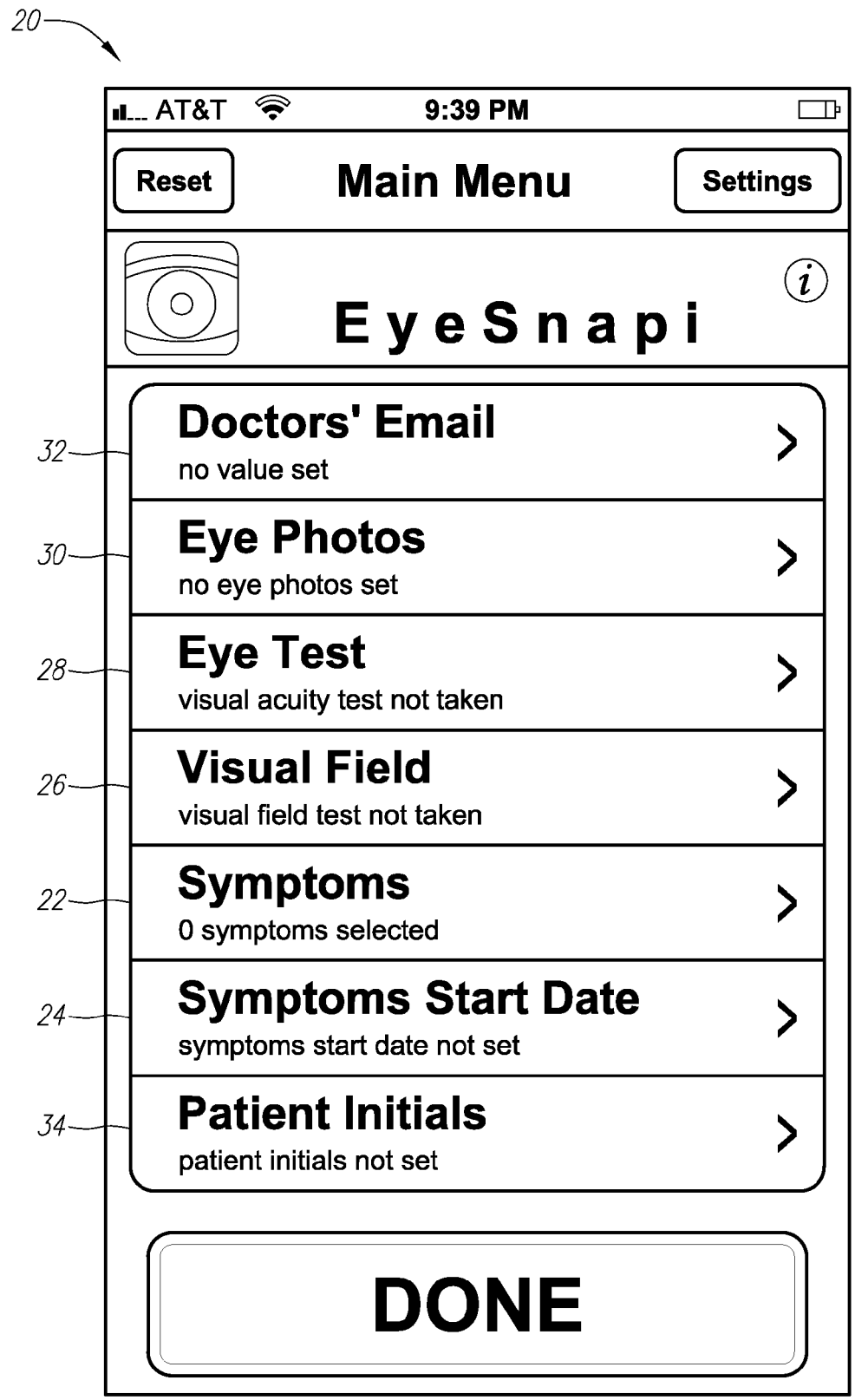
FIG. 2, illustrates an embodiment of a GUI designed to collect data for use in a medical diagnosis.

FIG. 2 illustrates an embodiment of a GUI 20 designed to collect data for use in a medical diagnosis. The GUI 20 in FIG. 2 is directed to collecting data for use with a diagnosis of the eye but in other embodiments, the GUI may be designed to collect data for some other health area. In other embodiments, the GUI may be a more general GUI designed to be used with numerous health areas.

The data for use in a medical diagnosis may come in many forms. The data may include pictures, video, text, selections from preexisting lists, sound or voice recordings, or any other type of data that may be useful in helping the medical professional provide a diagnosis and/or prescription.

In the embodiment shown in FIG. 2, the GUI 20 includes a number of fields or links to collect data for use in a medical diagnosis. For example, GUI 20 includes a link for: Symptoms 22, Symptoms Start Date 24, Visual Field 26, Eye Test 28, and Eye Photos 30. In other embodiments, other types of data may be collected.

In addition to data specifically designed to facilitate a diagnosis, the GUI 20 may include other data fields. For example, in some embodiments, the GUI 20 may include data fields to allow a medical professional's contact information to be entered. In the embodiment of FIG. 2, a data field allows a user to enter a doctor's email 32. In other embodiments, other types of contact information may be entered such as phone numbers, fax numbers, URLs or other types of contact information.

The embodiment of the GUI shown in FIG. 2 also includes a data field for user authorization 34. In the embodiment shown in FIG. 2, the user authorization 34 is the patient's initials, however in other embodiments, patient authorization may be in other forms such as signatures, digital signatures, approval buttons or the like. For example, the patient 11 may have a password or other type of authorization that is required to be entered.

Although FIG. 2 shows a number of different data fields, other embodiments may include more data fields or fewer data fields. In addition, other embodiments may include other categories of data. For example, data the medical professional may need in order to properly treat the patient but not specifically related to the diagnosis may also be entered. The data may be related to the medical history of the patient, general information about the patient, current drugs or other prescriptions the patient is taking, or any other type of relevant data. In other embodiments, disclaimers, liability releases, or any other type of legal paperwork may also be included in the data received or entered by the patient.

In a preferred embodiment, the patient may have data on file with the medical professional's office or saved locally on the mobile device or remotely on a server that is accessible via the mobile device. In such an embodiment, the data may be used to pre-populate forms or other patient required inputs. In some embodiments, the patient may be asked to confirm that the pre-populated data is still accurate before it is submitted.

One method of collecting data for use with a medical diagnosis is to take pictures, photographs or digital images of the medical condition, area in question, or ailment. For example, the embodiment of FIG. 2 includes a data field for Eye Photos 30. If a patient has an ailment or medical condition with respect to one or both eyes, say "pink eye" for example, the patient 11 may take photos of his/her eyes to send to a medical professional 15.

The embodiment shown in FIG. 2 includes a plurality of data fields 22-34. In a preferred embodiment, a patient 11 may have to fill in all the data fields before being allowed to send the data to a medical professional 15. The GUI of FIG. 2 may indicate to the patient 11 which fields have already been filled in and which fields have yet to be filled in. In other embodiments, only a portion of the data fields may have to be filled in before the patient is allowed to communicate with a medical professional 15.

Figure 3:
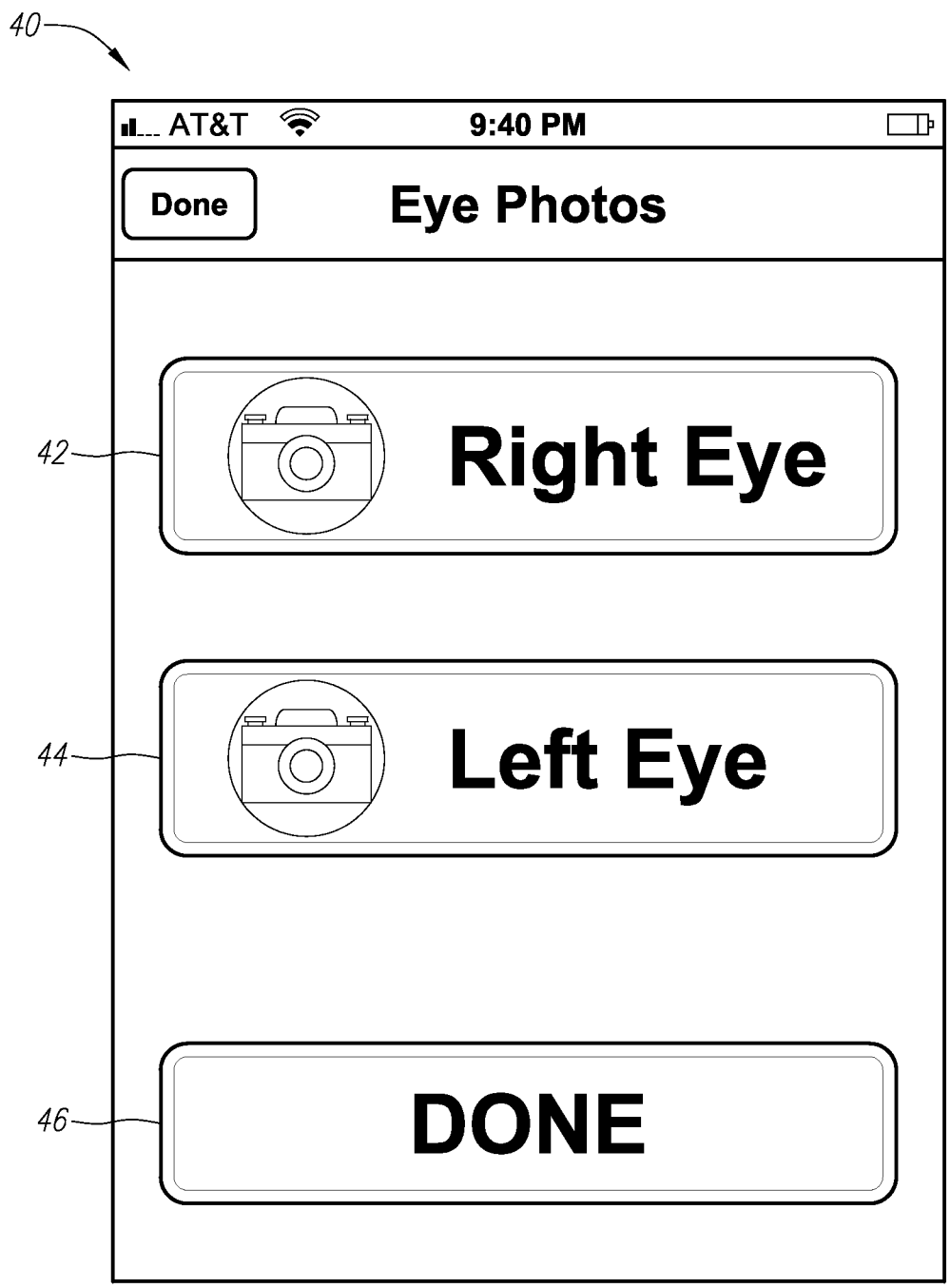
FIG. 3 illustrates a GUI for selecting a particular part of the body to photograph.

In the embodiment shown in FIG. 2, when a patient selects on the data field for Eye Photos 30, a new screen appears which is shown in FIG. 3. FIG. 3 illustrates a GUI for selecting a particular part of the body to photograph. In the embodiment of FIG. 3, the part of the body is the eye. When the patient selects the right eye button 42, a new GUI screen appears that allows a patient 11 to either take a picture of his/her right eye using the camera of the mobile device 13, or select an already existing photo. If the patient 11 selects an already existing photo, the photo may have been taken with the camera of the mobile device 13 or may have been taken with some other camera. Selection of the left eye may proceed in a similar fashion by selecting the button for the left eye 44. Once the patient 11 is satisfied with the photographic data he/she has collected, he/she may select the done button 46. The photographic data may then be stored for transfer to a medical professional 15 such as an optometrist.

In addition to photographs, some embodiments of the application may include video capture. For example, in one embodiment designed for use with an eye, video might be captured of the eye movement. In such an embodiment, the patient 11 may be requested to track an object on the screen while the video camera records the movement of the eye tracking the object. In yet another embodiment, the patient 11 may be instructed to look left or look right while video of the eye is being recorded.

In yet another embodiment, video might be used to capture a personal message from the patient for the medical professional. For example, the patient may record his/her explanation of his/her symptoms or how he/she is feeling.

Figure 4:
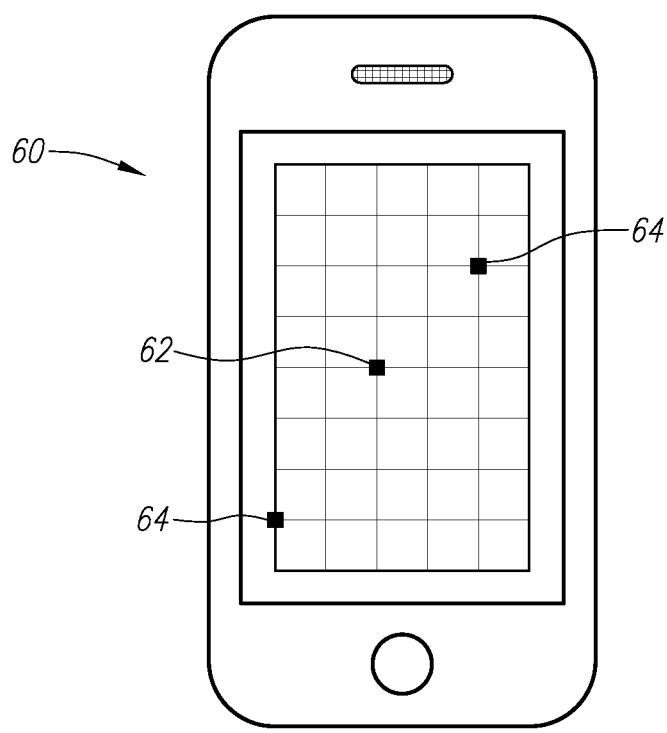
FIG. 4 illustrates one embodiment of a GUI designed to administer a visual field test.

In addition to photos, other embodiments may capture other data for use with a medical diagnosis. For example, in an embodiment designed for a medical condition related to the eye, a visual field test may be given. FIG. 4 illustrates one embodiment of a GUI 60 designed to administer a visual field test. As shown in FIG. 4, the visual field test may consist of a grid with a dot in the center 62. The patient 11 may be instructed to cover one eye, hold the mobile device 13 at arms length, and look at the dot in the center 62 of the grid. While focusing on the dot 62, the patient 11 should note and indicate the areas on the display where blind spots may appear. The location of the marks indicated by the patient may be visually referenced by a spot or other marker 64. The same process may be repeated for both eyes. In mobile devices 13 that include a touch screen display, the patient 11 may simply touch the screen where blind spots appear. On other mobile devices 13 that do not include a touch screen display, the patient 13 may indicate the area where blind spots appear by navigating a cursor.

In other embodiments, other forms of a visual field test may be used. In another embodiment of a visual field test, the user may be instructed to stare at the middle of the display of the mobile device and then the screen may flash small spots of light surrounding the center. The patient is instructed to indicate when he/she sees the discrete flash. By keeping track of the flashes the patient does not indicate, the software application may track blind spots in the patient's field of vision.

Figure 5:
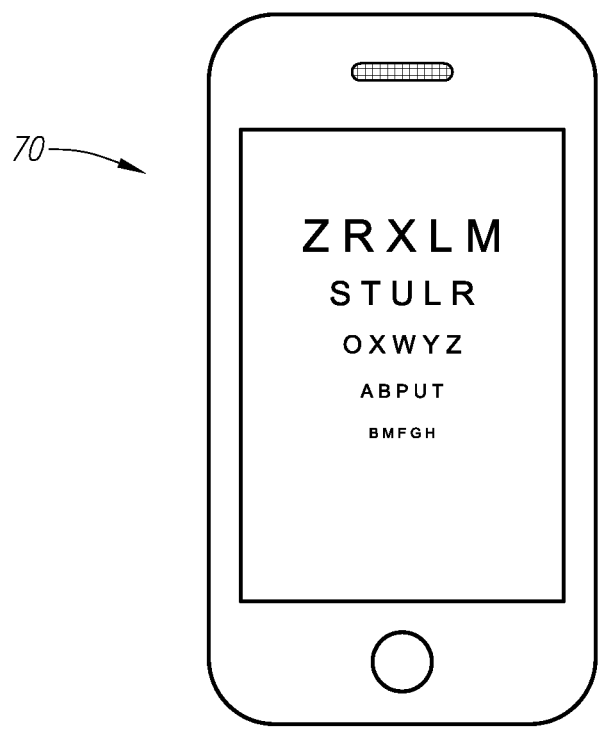
FIG. 5 illustrates one embodiment of a GUI for use in administering a visual acuity test.

An eye test is another form of data that may be collected in embodiments that are directed to medical conditions of the eye. The eye test may be a visual acuity test such as the one that is often administered at an eye doctor's office. FIG. 5 illustrates one embodiment of a GUI 70 for use in administering a visual acuity test. In the embodiment shown in FIG. 5, a number of letters are displayed in rows across the screen of the mobile device. Each row of letters below the previous row gets progressively smaller in size. The patient 11 is instructed to close or cover one eye, hold the mobile device at arm's length, and select the smallest row of letters that may be clearly seen. In a preferred embodiment, the letters may be designed to appear as a specific size on the screen of the mobile device such that the visual acuity of the patient reading the letters may be calculated based on the smallest row he/she can read while holding the phone at arm's length. In making the calculation, the patient's height may be used to factor into the calculation and calculate an arm's length. In other embodiments, the length of the patient's arm may be approximated.

Other types of data acquisition that may be beneficial in diagnosing medical conditions related to the eye include a Maddox Red Test. In performing the Maddox Red Test, the mobile device may shine a light consisting of both the bar and dot and the patient may be asked particular questions about what he/she perceives. Based on the patient's answers, a diagnosis about ocular alignment may be deduced.

Returning to FIG. 2, other forms of data for use in allowing a medical professional to make a diagnosis and/or administer a prescription may include the user's specific symptoms in connection with the medical condition. In some embodiments, the user may simply be able to type into a text box a description of his/her symptoms. In another embodiment, the user may be directed to a list of common symptoms and asked to select any number of common symptoms that apply. In other embodiments, a text entry box for describing symptoms and a means for selecting a number of common symptoms may both be used. In other embodiments, other methods of describing symptoms associated with a patient's medical condition or selecting symptoms from a list may be used.

Figure 6:
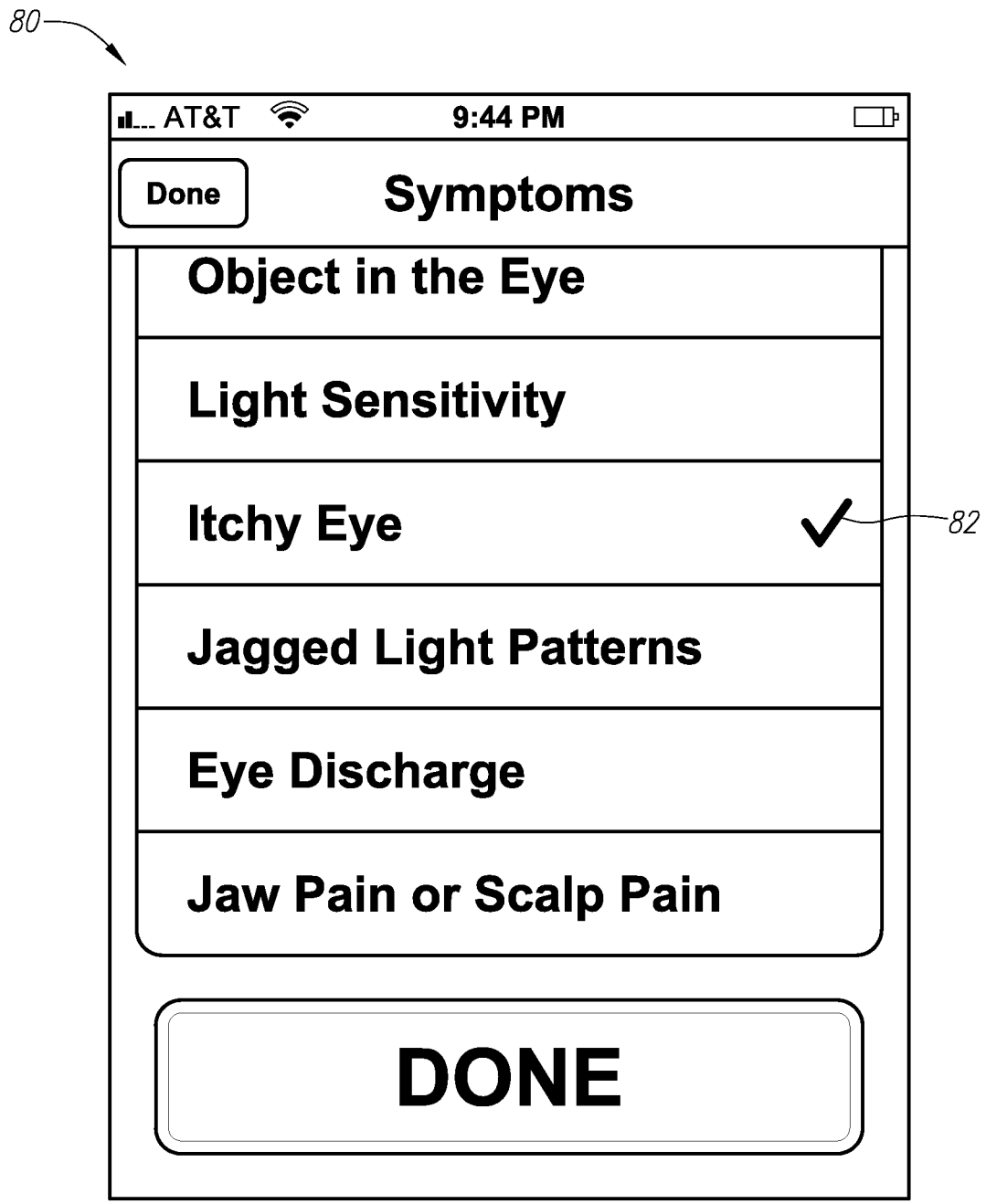
FIG. 6 illustrates one embodiment of a GUI for selecting symptoms from a list of common symptoms.

FIG. 6 illustrates one embodiment of a GUI for selecting symptoms from a list of common symptoms. For example, symptoms related to a medical condition associated with an eye may included: trauma, pain, blurry vision, double vision, loss of vision, curtain over vision, floaters or flashes, red eye, object in eye, light sensitivity, itchy eye, jagged light patterns, eye discharge (pus), and jaw pain or scalp pain. In other embodiments, additional or fewer symptoms may be included in the list. Lists designed for other medical conditions or for more general medical conditions may include completely different symptoms. Furthermore, the list may be tiered such that a patient selects from a broad category of medical conditions and then is presented with lists of symptoms that decrease in scope and are related to the specific medical condition selected.

In a preferred embodiment, the patient 11 may select a plurality of symptoms associated with his/her medical condition. The GUI may display the selected choices in a number of different ways such as putting a check 82 next to the selected symptoms. In other embodiments, the symptoms may be selected in other ways.

In addition to selecting the symptoms, some embodiments may also allow a patient 11 to enter information about when the symptoms started or where first noticed by the patient. In some embodiments, the patient 11 may simply type in a text box when he/she first noticed the symptoms. In a preferred embodiment, the patient 11 may select from a list of time periods when the symptoms where first noticed. For example, the list of times when the symptoms were first noticed may include: 1 hour ago, several hours ago, 1 day ago, several days ago, 1 week ago, several weeks ago, 1 month ago, more than a month ago, or no symptoms.

Once the data for use in diagnosing the medical condition is collected, it may be sent to a medical professional 15. The data may be sent via email, fax, ftp, http, or any other transfer method. In some embodiments, the data may be sent securely by encrypting the data and/or sending the data over a secured connection. In other embodiments, no data security may be used.

Figure 7:
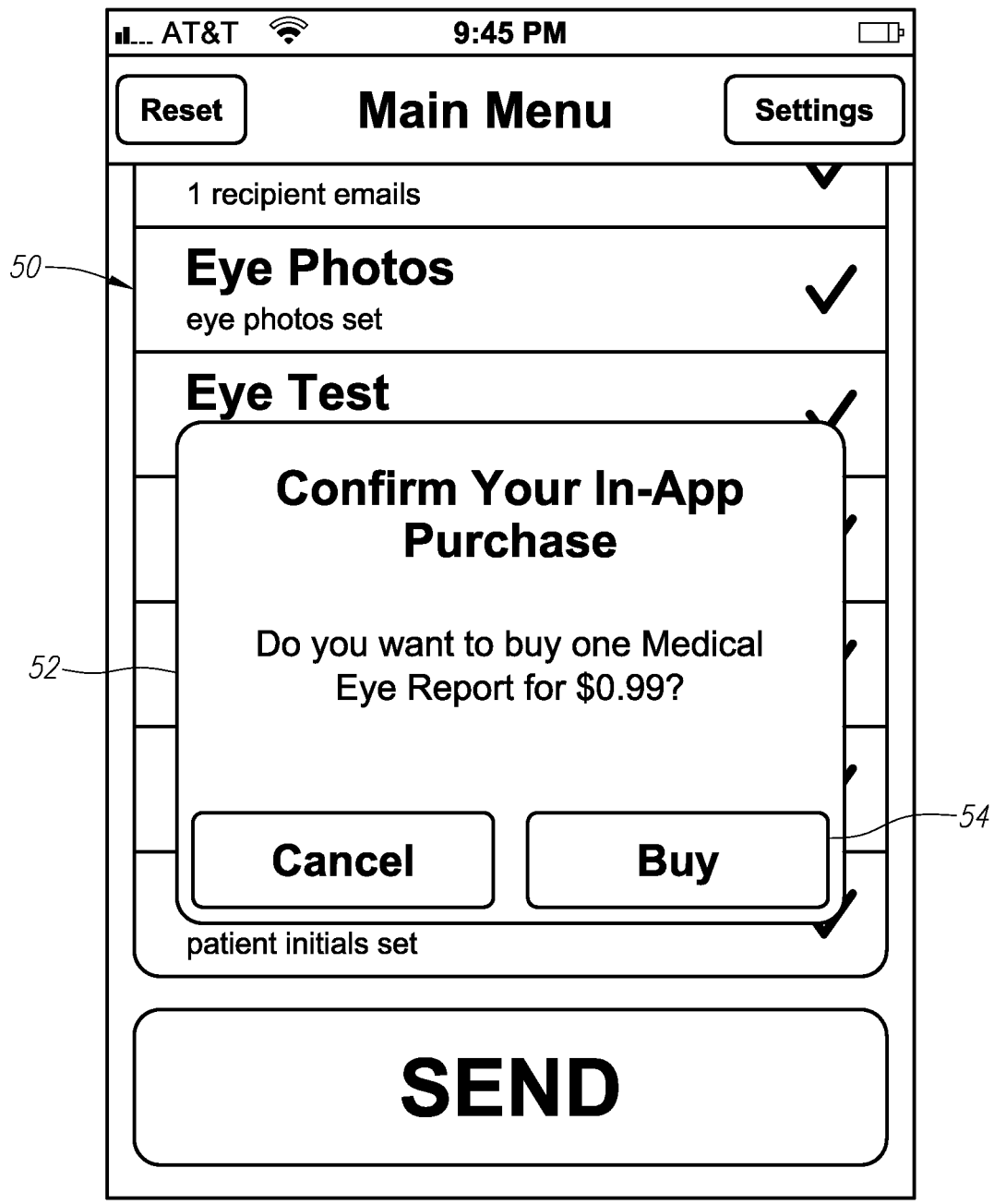
FIG. 7 illustrates one example of a GUI for purchasing a single diagnosis and/or prescription.

In various embodiments of the software application, various different monetization schemes may be employed. In one embodiment, once the patient 11 has entered all the required data, the patient 11 may submit the data to a medical professional 15. When the patient 11 submits the data, the patient may be asked to purchase a response. FIG. 7 illustrates one example of a GUI 50 for purchasing a single diagnosis and/or prescription. In FIG. 7, the patient 11 is requested to buy one Medical Eye Report for a fee ($0.99) in a pop-up window 52. The fee amount of $0.99 is just one example, and other amounts may be used. For example, more expensive amounts may be used for a diagnosis or different amounts for different levels of service.

If the user selects the buy button 54, the fee may be billed to a credit card already on file or the patient 11 may enter credit card information. In various embodiments, numerous forms of payment may be accepted such as PayPal®, digital checks, and other electronic payment forms.

In a preferred embodiment, the medical diagnosis may be integrated with the patient's insurance. In such an embodiment, the patient may be prompted to accept a co-pay amount which may be charged to the patient, and the remainder of the bill may be automatically sent to the patient's health insurance provider.

In other embodiments, other monetization schemes may be used. For example, in some embodiments, the patient 11 may pay for a block of diagnoses and/or prescriptions for a fixed fee. In other embodiments, the patient may pay for the transmission of the data and pay an additional fee for a diagnosis or prescription. In yet another example, the patient 11 may sign up for a period of time for a limited or unlimited number of diagnoses and/or prescriptions. In other embodiments, advertisements may be used to generate revenues. Advertisements may pop up automatically, may be integrated into the software, or may pop up only once the user requests a diagnosis.

In yet another embodiment, the patient 11 may be charged for purchasing the software application which gives the patient 11 a limited number of diagnoses and/or prescriptions. Once the limited number of diagnoses and/or prescriptions are used, the software application may become inactive until the patient 11 pays again. In some embodiments, multiple monetization schemes may be used in combination. For example, patient 11 may purchase a single diagnosis and/or prescription, and advertisements may be shown at the same time.

In some embodiments, the software application may be used as a marketing tool. For example, patient 11 may be sent coupons or vouchers for a free sample of a drug that may help his/her medical condition. For example, a patient may have a red itchy eye. The patient may be sent a coupon or voucher for a free sample of an eye drop such as Visine®. The patient may then be able to pick up the free sample at his/her local pharmacy or drug store, or the free sample may be mailed to the patient directly. This serves as a way to introduce potential customers to new products.

In some embodiments, the patient 11 may be asked to accept a liability agreement, disclaimer, or other legal paperwork. In some embodiments, acceptance of the agreement may only be required when the patient 11 actually requests a diagnosis. In other embodiments, the liability agreement may be presented to the patient 11 when the application begins. In other embodiments, the liability agreement may be presented to the patient 11 at other times. In still other embodiments, no liability agreement is used at all.

Although in some of the embodiments described above, medical conditions related to the eye are used as examples, the software application may be designed to function with other medical conditions. In some embodiments, an application designed to provide a remote diagnosis and/or prescription may be directed to medical conditions related to the skin.

Figure 8:
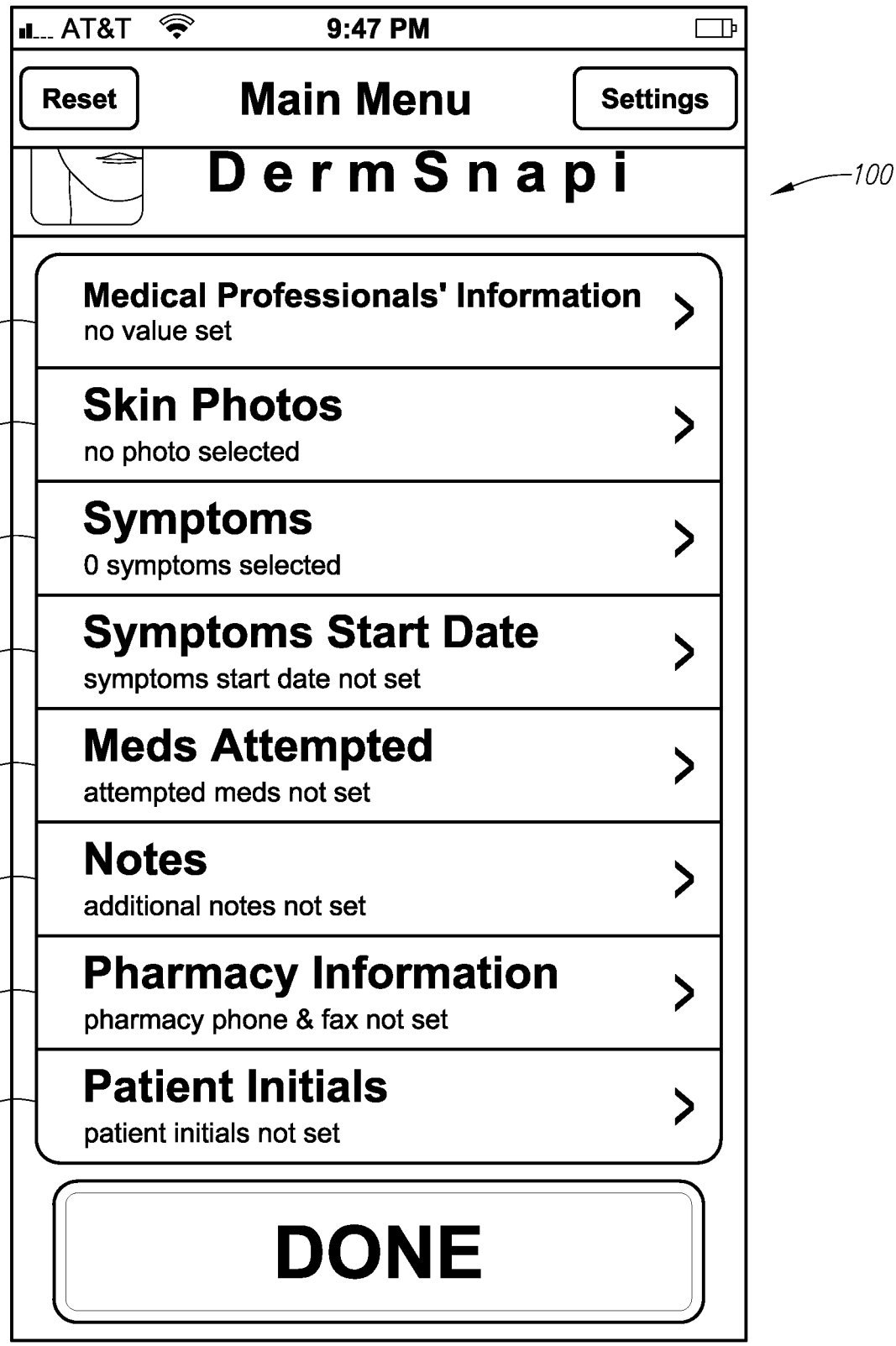
FIG. 8 illustrates an embodiment of a GUI designed to collect data for use in a medical diagnosis related to a skin condition.

FIG. 8 illustrates an embodiment of a GUI 100 designed to collect data for use in a medical diagnosis related to a skin condition. The GUI 100 includes a number of fields or links to collect data for use in a medical diagnosis. For example, GUI 100 includes links for: Symptoms 22, Symptoms Start Date 24, Meds Attempted 102, Notes 104 and Skin Photos 30. In other embodiments, other types of data may be collected. The data collected is designed to allow a medical professional 15 to make a diagnosis and/or give a prescription.

The embodiment shown in FIG. 8 also includes a field for Pharmacy Information 108. Pharmacy Information 108 may be any contact information for a pharmacy or pharmacies to which patient 11 wants to be directed. Pharmacy information may include phone numbers, fax numbers, or email addresses. In some embodiments, pharmacy information 108 may be used by the application to manage prescriptions. In other embodiments, pharmacy information 108 may be provided to allow the medical professional 15 to obtain additional information about the patient 11 such as information about the medical history of the patient 11.

Different embodiments designed for different medical conditions may include different symptoms. For example, an embodiment related to a skin condition may include symptoms such as: growing, changing colors, bleeding, tender, burning, itching, not improving, worsening, dry or scaly. Other embodiments may include other symptoms.

Figure 9:
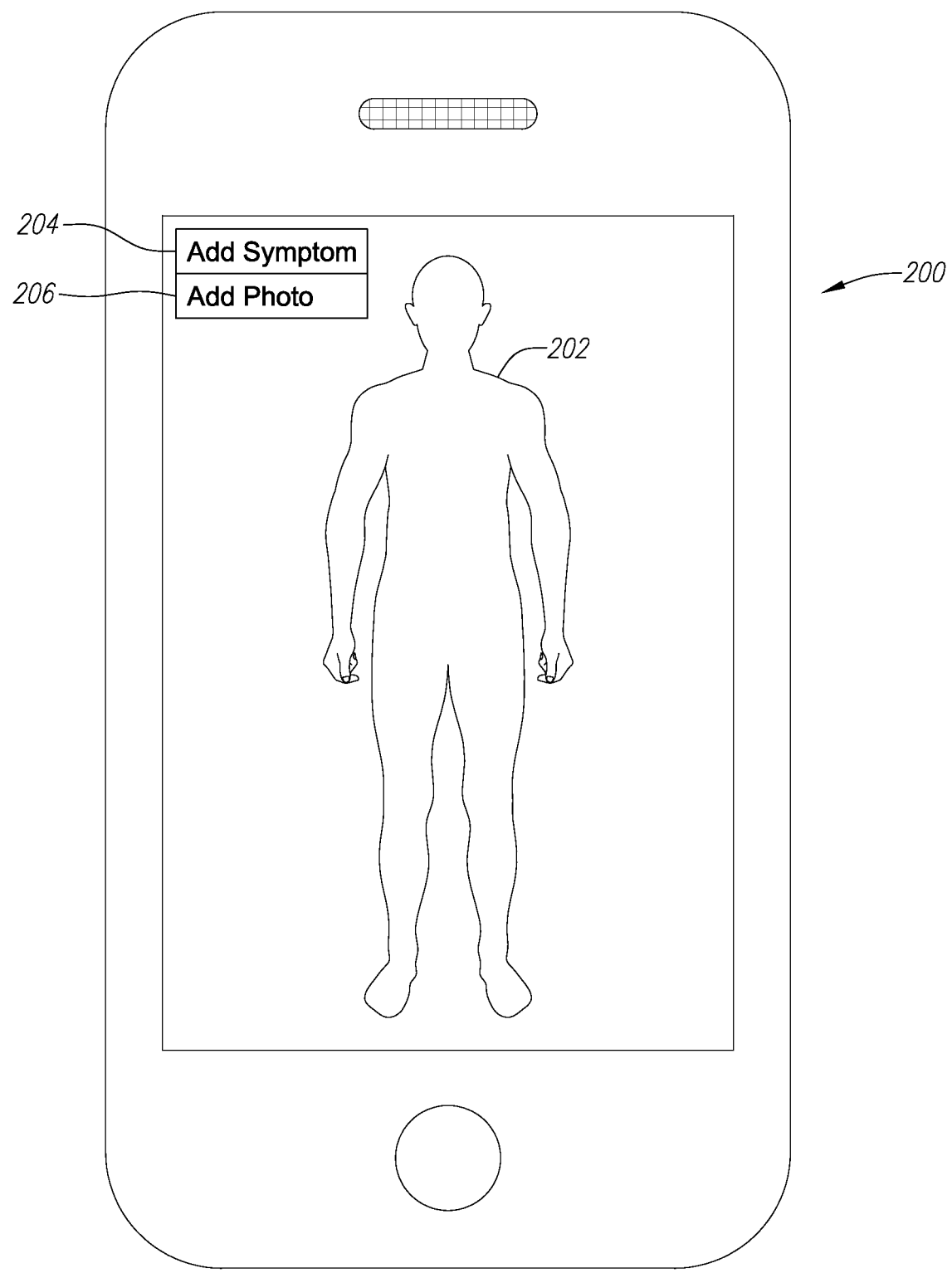
FIG. 9 illustrates an embodiment of a GUI for locating a medical condition on a body.

In various embodiments, different GUIs may be used to help collect the data for use in a medical diagnosis. For example, one embodiment of a GUI to help collect data for use in a medical diagnosis may include an image of a human body to allow the patient to locate where the medical condition is occurring. FIG. 9 illustrates an embodiment of a GUI for locating a medical condition on a body. As shown in the embodiment of FIG. 9, an image representative of a human body may be shown to the patient 11. The patient 11 may be instructed to select the area on the representation of the human body where he/she is experiencing a medical condition.

In some embodiments, once the patient selects an area on the representative body, a new image of only the local area of the body selected is presented to the patient 11 so that the patient 11 may select again and more precisely locate the medical condition. This process may be repeated as many times as necessary to allow the patient 11 to precisely locate the medical condition. For example, the patient 11 may select the left arm of the representative body shown in FIG. 9. After selecting the left arm, an image of only the left arm may be presented to the patient 11 to allow the patient 11 to select from the upper arm, elbow, left hand, lower arm, etc.

In certain embodiments, the patient 11 may indicate he/she is done locating the medical condition at any level of specificity. In other embodiments, the patient 11 may be forced by the GUI to go through a minimum number of selection screens to locate the medical condition.

In other embodiments, the GUI may provide a more interactive human body from which to select. For example, rather than a number of different screens, the patient 11 may be able to zoom in and out and pan around on the existing screen representing the body to more precisely locate the medical condition. In other embodiments, a patient 11 may even be able to rotate the body on the screen. In some embodiments, a three dimensional body may be represented by the GUI that may be interacted with by the patient 11 to provide data on the patient's medical condition. The patient 11 may rotate, pan and zoom the three dimensional body to locate areas on the body where a medical condition is occurring.

In some embodiments, data for use in diagnosing a medical condition may be associated with the location selected on the representative body. As shown in FIG. 9, the GUI may further include buttons 204 and 206 for adding symptoms and photos respectively. Once the patient 11 selects a location for the medical condition, the patient may associate either symptoms or a picture with that location by selecting the button. In some embodiments, the patient 11 may be able to repeat this process to associate various different pictures or symptoms with various different locations on the body.

In some embodiments, the methods and apparatuses described herein may be used to provide data for use in a diagnosis and/or prescription to multiple medical professionals. If multiple medical professionals receive the data, the patient 11 may receive only the first response, may be able to choose which professional he/she would like to respond, or may get a consensus response.

In an exemplary embodiment of a consensus response, the patient 11 may open the application and collect data of an existing medical condition, such as photos and symptoms, and send the data to multiple physicians. For example, the patient 11 may take a picture of a concerning mole. The mole may be examined by multiple physicians/specialists who choose a response and the response data is returned to the patient 11. For example, four out of five dermatologists chose this mole as completely harmless with its current appearance. One out of five dermatologists chose this mole to be appearing mildly atypical, follow for changes, but no biopsy necessary at this time.

In yet another embodiment, the software application may provide the ability to handle prescriptions for a patient. For example, the software application may track the patients current medication prescriptions, dosage, and number of refills. In some embodiments, the software application may further track the patient's medication and prescription history. For medication that needs to be taken periodically, the software application may remind the patient when it is time to take the medication with an alert, text message, alarm, email or other type of communication.

In some embodiments, the software application may facilitate the patient getting refills of a prescription. The software application may track and remind the patient when it is time to order a refill. The software application may further send a request to a pharmacy to process the refill. The request may be sent automatically or may be initiated by the patient. If no refills remain, the request may be sent to a physician instead of a pharmacy to try and obtain an extended prescription.

In various embodiments, the data for medical diagnosis may be routed to the medical professionals in a number of ways. For example, all the requests for diagnosis may be posted on a central website, and medical professionals may securely log onto such a website and provide as many diagnoses as they wish. In such an embodiment, the medical professional may receive compensation for each diagnosis.

In another embodiment, the medical professionals may bid an amount to provide a diagnosis and the request may be routed to the lowest bidder. In yet another embodiment, the medical professionals may not receive monetary compensation at all for providing diagnosis but may be incentivized by other methods.

In other embodiments, requests for diagnosis may only be routed directly between the patient 11 and his/her existing medical professionals 15. In yet other embodiments, patient 11 using the software application may be able to browse through a list of medical professionals 15 qualified to make the diagnosis, and may select the medical professional 15 of his/her choice.

In another embodiment, the data may be uploaded into a compatible electronic medical record (EMR) system using an application programmers interface (API). The data may then be uploaded directly into the patient's chart. The connection may be preferably encrypted and comply with Health Insurance Portability and Accountability Act (HIPAA).

Figure 10:
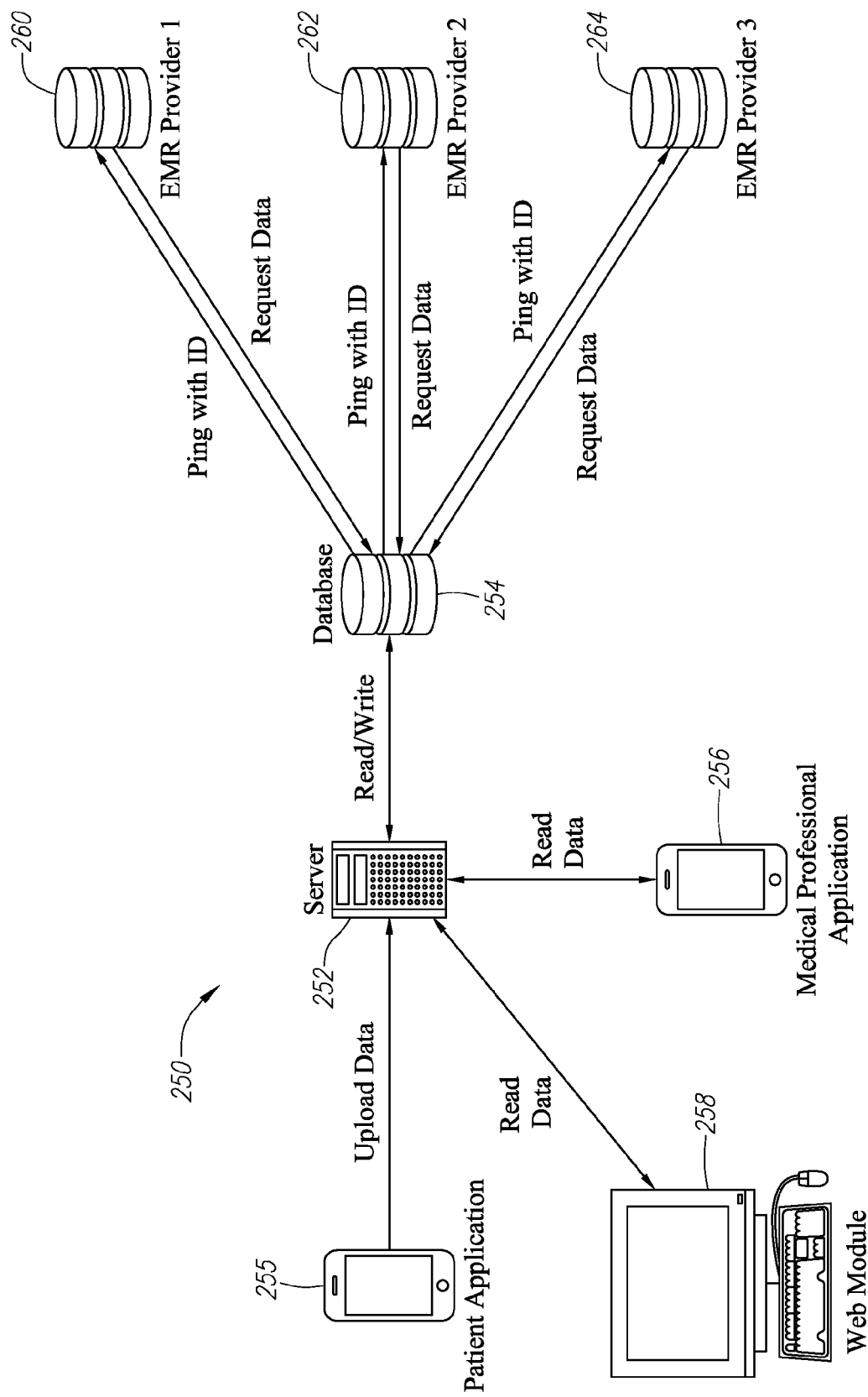
FIG. 10 illustrates one embodiment of network for use with providing a remote medical diagnosis that is integrated with an EMR system FIG. 11 Legend for FIG. 11A and FIG. 11B.

FIG. 10 illustrates one embodiment of network 250 for use with providing a remote medical diagnosis that is integrated with an EMR system. The embodiment shown as network 250 includes server 252, database 254, EMR providers 260, 262, and 264, patient application 255, doctor application 256 and web module 258. In the embodiment shown in network 250, the server 252 facilitates the exchange of data between the doctor and the patient. The patient may collect data for use in allowing a medical professional to make a diagnosis and/or prescription and send the data to the server 252. If the data sent by the patient has all the necessary information, the server 252 may pass it directly on to a doctor. However, in other embodiments, the server 252 may supplement the information provided by the patient with information from a database 254.

In some embodiments, the database 254 is in communication with an EMR provider or plurality of EMR providers 260, 262 and 264. In some embodiments, when a request for a diagnosis is received from a patient, the data may be recorded in the database 254. The data may be tied to the patient via a patient ID or some other form of identifier. The data may be further passed to an EMR provider 260, 262 and 264 for recording by the EMR provider.

In addition to recording the data provided by the patient, in other embodiments, the server may take the data provided by the patient and supplement the patient data or cross-check the patient data with data available in the database 254 or data available from an EMR provider 260, 262 and 264.

As may be seen in FIG. 10, the medical professional may have access to the data in the database 254 and other associated data including data from the EMR providers 260, 262 and 264 via a number of interfaces. For example, the medical professional may have an application 256 running on his/her medical device. In other embodiments, the medical professional may have access to the data via a web module 258. In a preferred embodiment, the interface used by the medical professional includes secure access and/or verification to make sure only medical professional may access the data.

The medical professional's interface may not only allow the medical professional to access data, it may also provide notification to the medical professional about pending or recent requests. Although in the embodiment illustrated in FIG. 10 the server 252 and the database 254 are shown as separate entities, the server and the database may reside on the same computer in some embodiments.

Figure 11B:
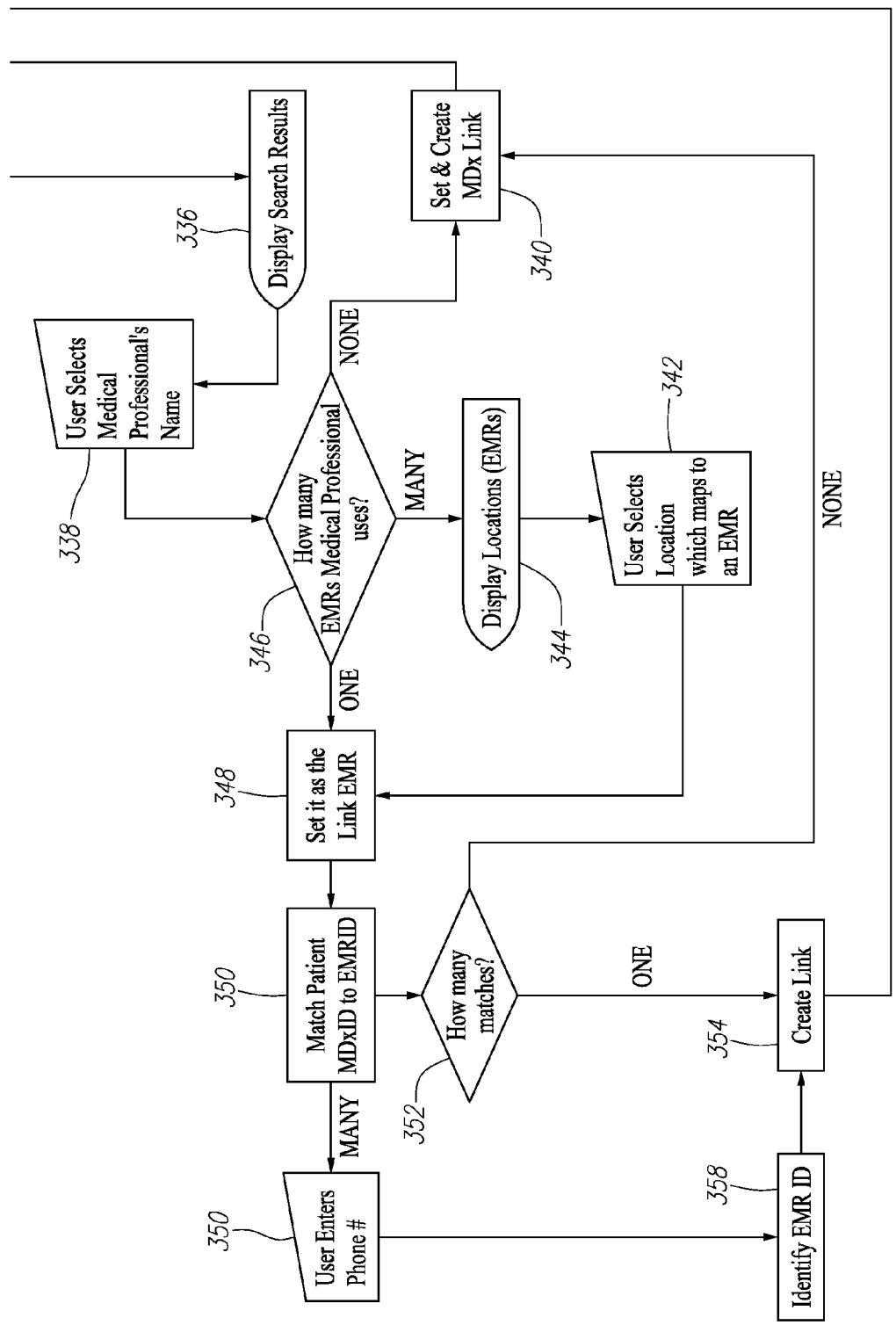
FIG. 11B illustrates the bottom half of a flow chart of one embodiment of a process that communicates data for use in a diagnosis and/or prescription to a medical professional.

FIG. 11 illustrates a legend for FIGS. 11A and 11B. FIGS. 11A and 11B illustrate a flow chart of one embodiment of a process 300 that communicates data for use in a diagnosis and/or prescription to a medical professional. In the process 300 shown in FIG. 11A, a patient starts 302 by launching a software application 304 on an electronic device. In a preferred embodiment, a mobile device is used. The patient uses the electronic device in combination with the software application to input and collect data 306 for use in allowing a medical professional to make a diagnosis and/or a prescription.

Once the data is collected, the data may be transferred to a medical professional. If the patient has the contact information of the medical professional, the patient may send the data directly to the medical professional. For example, the patient may compose and email 310 and send the data to the medical professional. As one alternative to sending an email to the medical professional, the patient may interface with the medical professional through an EMR system 314.

In the embodiment shown in FIG. 11, the EMR system may facilitate sending the data to a medical professional 314. The EMR system may first determine whether the patient is signed in 316 and has a user account 318. If the patient does not have a user account, the EMR system may create a user account 320. Once the user account is created, the patient may be signed into the EMR system using the patient's email, or other login ID, and a password 322.

Once the patient is signed in, the EMR system may check to see if the patient has any links to medical professionals. If the patient has links to a medical professional, the patient may select the link 328 and the report may be sent to the medical professional via the information in the link 330. The link may be a URL or record locator in the EMR or any other type of link to a medical professionals contact information. In some embodiments, the EMR system may also add a record to the patient's EMR account to track the request for a diagnosis and/or prescription and make a electronic record of the data conveyed to the medical professional If the patient does not currently have any links to a medical professional associated with his/her login ID, the patient may be prompted to add a link to a medical professional 326. The patient may be presented with a search interface 334. The patient may search for a medical professional using any method including by name 334. In other embodiments, a patient may search for a medical professional by geographic location, by the type of insurance coverage the medical professional accepts, by cheapest service, by user rating, or by any other criteria. In other embodiments, the patient may search for medical professionals using any combination of factors.

Once the patient selects a medical professional, the system may determine which EMR to use with the patient. Transitioning to FIG. 11B, the system may first determine the number of EMR's the medical professional uses 346. If the medical professional uses more than one EMR (for example a different EMR system for various different offices), the system may display the location of the various EMRs 344 to allow the patient to select the most appropriate one 342. If only one EMR is associated to the medical professional, that EMR may be selected.

Once an EMR is selected, the patient's MDxID, which is associated with the patient at the software application level running on the electronic device, may be matched to the EMR-ID 350. The match may be done using the patient's phone number, login ID, name, social security number, or any other identifying information or combination thereof. Once the EMR-ID is identified 358, a link to the information needed to send the data to the medical professional may be established and the data sent 330.

The methods and apparatuses described herein may be used in any location. For example, in many embodiments, the methods and apparatuses described herein may be used in the waiting room of the medical professional's office. This may allow more efficient use of time for both the medical professional and the patient. In such embodiments, the patient may be able to perform many of the simple examinations himself which saves the medical professional's time when actually seeing the patient.

In addition, the embodiments disclosed herein may include or be used with external devices designed to work with a mobile device. For example, a stethoscope, blood sugar monitor, heart monitor, blood pressure monitor, or other medical device may be designed to work in conjunction with a mobile device and may work with the methods and apparatuses disclosed. The external devices may be used to help the patient obtain data for use in a diagnosis. As just one example, a patient with diabetes may obtain information about his/her current blood sugar levels and upload that data to a medical professional for diagnosis. In some embodiments, the patient's blood sugar levels may be obtained by an external device designed to interface with the patient's mobile device.

For embodiments in the form of a software application for use with a mobile device, distribution may be facilitated or controlled through popular mobile device application distributions methods such as the Apple App Store® or Amazon's Marketplace®. In yet other embodiments, the application(s) for the various mobile devices may be downloaded from the Internet or other accessible location. In still yet other embodiments, the application may be pushed to the mobile device. For example, a patient coming within a certain proximity to the medical professional's office, such as in the waiting room, may have the software application pushed to his/her device. This may require confirmation by the user to opt-in to the software application.

In still other embodiments, a mobile device specifically for use with acquiring medical information may be designed. Such a device may be branded and sold. In some embodiments, the mobile device specifically designed for acquiring medical information may include special hardware for acquiring medical information. As just one example, a mobile device, such as a smart phone, may also be designed to allow a patient to test his/her blood sugar levels using the mobile device. The information may then be forwarded to a medical professional for diagnosis, review and/or prescription.

The foregoing description of embodiments has been presented for the purposes of illustration and description. It is not intended to limit the embodiments to the precise forms disclosed. Many modifications and variations are possible in light of the above teachings. It is intended that the scope of embodiments not be limited by this detailed description, but by the claims and the equivalents to the claims that are appended hereto.

What is claimed is:

1. A method of enabling a remote medical diagnosis of a medical condition comprising the steps of:
   causing a display of a mobile phone to display a graphical image designed for use in the medical diagnosis of an eye condition;
   collecting data on the mobile phone related to a perception of the graphical image;
   causing an object to be displayed on the display of the mobile phone while recording video of a user's eye tracking the object;
   receiving a picture or video of an eye condition from a camera on the mobile phone;
   transmitting the picture or video and data from the mobile phone to a medical professional over a wireless network;
   establishing payment for a medical diagnosis over the wireless network via the mobile phone; and
   receiving, on the mobile phone over the wireless network, only after the establishing payment step, the medical diagnosis from the medical professional.

2. The method of claim 1, wherein the data further includes at least one symptom of the eye condition.

3. The method of claim 1, wherein the medical professional is an optometrist.

4. The method of claim 1, wherein the picture or video is communicated to the medical professional via text or email.

5. The method of claim 1, further comprising the step of transmitting a video that includes a personal message for the medical professional.

6. The method of claim 1, further comprising the step of receiving a treatment suggestion from the medical professional.

7. The method of claim 1, further comprising the step of causing the display of the mobile phone to display a medical disclaimer required to be accepted by a user.

8. The method of claim 1, further comprising the step of causing the display of the mobile phone to display a single screen that allows selection of additional screens for Symptoms, Visual Field, Eye Test and Eye Photos.

9. The method of claim 8, further comprising the step of receiving a patient authorization.

10. The method of claim 9, wherein the data further comprises medical history information and drugs or prescriptions currently being taken.

11. The method of claim 1, further comprising the step of displaying a screen on the mobile phone allowing selection between the right eye and left eye.

12. The method of claim 1, wherein the graphical image is a visual field test.

13. The method of claim 1, wherein the graphical image is a visual acuity test.

14. The method of claim 1, wherein a listed of symptoms is displayed on the mobile phone, the list of symptoms including pain, blurry vision, double vision, loss of vision, floaters, red eye and object in eye.

15. The method of claim 1, wherein payment is established for a single diagnosis.

16. The method of claim 15, wherein payment is a co-pay amount based on a health insurance policy.

17. The method of claim 16, wherein a portion of the payment other than the co-pay is automatically sent to a health insurance agency.

18. The method of claim 1, wherein payment is established for a plurality of diagnosis.

19. A non-transitory computer readable medium containing program instructions for providing a diagnosis by a medical professional, wherein execution of the program instructions by one or more processors of a mobile device causes the one or more processors to perform a method comprising the steps of:
   causing a display of a mobile phone to display a graphical image designed for use in the medical diagnosis of an eye condition;
   collecting data on the mobile phone related to a perception of the graphical image;
   causing an object to be displayed on the display of the mobile phone while recording video of a user's eye tracking the object;
   receiving a picture or video of an eye condition from a camera on the mobile phone;
   transmitting the picture or video and data from the phone to a medical professional over a wireless network;
   establishing payment for a medical diagnosis over the wireless network via the mobile phone; and
   receiving, on the mobile phone over the wireless network, only after the establishing payment step, the medical diagnosis from the medical professional.

20. The non-transitory computer readable medium of claim 19, wherein execution of the program instructions by one or more processors of a mobile device causes the one or more processors to perform a method wherein the data includes at least one symptom of the medical condition.

21. The non-transitory computer readable medium of claim 19, wherein the picture or video is transmitted to the medical professional via text or email.

22. The non-transitory computer readable medium of claim 19, wherein execution of the program instructions by one or more processors of a mobile device causes the one or more processors to perform a method further comprising the step of receiving, on the mobile phone, a treatment suggestion from the medical professional.

23. The non-transitory computer readable medium of claim 19, wherein execution of the program instructions by one or more processors of a mobile device causes the one or more processors to perform a method further comprising the step of transmitting a video that includes a personal message for the medical professional.

* * * * *